United States Patent [19]

Hoppe et al.

[11] Patent Number: 4,600,539
[45] Date of Patent: Jul. 15, 1986

[54] O/W EMULSIFIERS FOR COSMETIC PURPOSES

[75] Inventors: Udo Hoppe, Hamburg; Jochen M. Quack, Eppstein; Alwin Reng, Kelkheim; Herbert Stühler, Burgkirchen/Alz; Klaus-Peter Wittern, Schenefeld, all of Fed. Rep. of Germany

[73] Assignees: Beiersdorf AG, Hamburg; Hoechst AG, Frankfurt, both of Fed. Rep. of Germany

[21] Appl. No.: 661,004

[22] Filed: Oct. 15, 1984

[30] Foreign Application Priority Data

Oct. 27, 1983 [DE] Fed. Rep. of Germany ....... 3338890

[51] Int. Cl.$^4$ ................................................ C11C 3/02
[52] U.S. Cl. ........................... 260/410.7; 252/522 A; 260/410.6
[58] Field of Search ......................... 260/410.7, 410.6; 252/522

[56] References Cited

U.S. PATENT DOCUMENTS 1,990,615  2/1935  Rodrian et al. .................. 260/410.6
3,859,318  1/1975  Lesuer .............................. 260/410.7
4,363,763  12/1982  Peterson ........................... 260/410.7

OTHER PUBLICATIONS

Motiuk Wool Wax Acid Review "J. Amer. Oil Chem. Soc." vol. 56, Feb. 1979.
Motiuk Wool Wax Alcohol Review—J. Amer. Oil Chem. Soc. vol. 56, Jun. 1979.
The Merck Index, Ninth Edition p. 704 Merck and Co., Inc. 1976.
Nonionic Surfactants vol. 1 pp. 416–417, Marcel Dekker, Inc. 1967, by L. W. Burnette.
Surface Active Ethylene Oxide Adducts by N. Schonfeldt 1970, Pergamon Press pp. 534–535.

Primary Examiner—Werren B. Lone
Attorney, Agent, or Firm—Sprung, Horn, Kramer & Woods

[57] ABSTRACT

The invention relates to novel O/W emulsifiers obtainable by reacting one mole of esters of wool wax acids and glycerol, in particular partial esters, with 0.5 to 30 moles of ethylene oxide, a process for the preparation of these novel products and cosmetic agents containing these in an amount of 1 to 15% by weight, based on the total formulation.

6 Claims, No Drawings

O/W EMULSIFIERS FOR COSMETIC PURPOSES

The invention relates to novel oil-in-water (O/W) emulsifiers, a process for their preparation and cosmetic formulations containing them.

It is known that cosmetic formulations which contain wool wax or wool wax derivatives easiliy penetrate into the skin when applied thereto and have the effect of softening the skin and rendering it supple, and are thus useful skin care agents. This is largely to be attributed to the fact that the base substance, i.e. wool wax (lanolin), which is obtained from sheep's wool, is the most closely related of all the natural base substances to the fats of human skin and hair in respect of its chemical composition and its physiological properties (J. S. Jellinek "Kosmetologie" ["Cosmetology"], 2nd edition, Dr. Alfred Huthig Verlag Heidelberg (1967), page 151).

Products with excellent properties are obtained using W/O emulsions prepared from wool wax alcohols obtained by hydrolysis of wool wax, as a result of the outstanding emulsifying properties of the wool wax alcohol, and these products are particularly stable in the form of creams, ointments and liquid emulsions and as a result have found wide use.

W/O emulsions can also be prepared, as described in German Pat. No. 2,023,786 or the corresponding British Pat. No. 1,341,094, with the esters from wool wax acids with glycerol, produced by the usual esterification process with continuous separation of water at elevated temperature. Particularly the partial esters, which are obtainable by stopping the reaction before all free hydroxyl groups of the glycerol are esterified, have at least an equivalent but in most cases superior emulsifying capacity to the wool wax alcohols. These emulsions, besides having a good stability, are distinguished by a particularly attractive luster. Compared with other emulsifiers based on wool wax, these esters have the great advantage that they can be obtained inexpensively in a simple manner by a procedure in which the wool wax acids which are obtained in a considerable amount as an undesirable by-product in the hydrolysis of wool wax to obtain wool wax alcohols and for which no real use has hitherto been found, in spite of a great deal of effort, are esterified with glycerol. As is known, glycerol is also a by-product which is obtained in relatively large amounts on hydrolysis of vegetable and animal fats in the course of soap production.

Both the wool wax alcohols and the wool wax acid glycerol esters are pronounced W/O emulsifiers, which are readily soluble in mineral oils, isopropylmyristate, castor oil and similar oily substances, but are insoluble in water.

Since at least a limited water-solubility of the emulsifier is desirable for the preparation of particular cosmetic products, the object of the invention was to discover compounds, and to provide processes for their preparation, which exhibit an adequate water-solubility, whilst retaining the particularly advantageous properties of formulations containing wool wax derivatives, the surface-active properties being modified.

Another object of the invention was to open up new fields of application for the wool wax acid glycerol esters obtainable in a simple and inexpensive manner, in particular the partial esters of glycerol with wool wax acids.

It has now been found, and these objects have thereby been achieved, that products which have a good water-solubility and moreover are pronounced O/W emulsifiers can be obtained from the esters of wool wax acids with glycerol, in particular the partial esters, by polyethoxylation (reaction with ethylene oxide). The molar ratio between the wool wax acid glycerol esters and ethylene oxide can be varied within wide limits in the reaction, depending on the desired properties of the reaction products.

The invention thus relates to novel O/W emulsifiers for cosmetic purposes which are based on polyethoxylated wool wax derivatives obtainable by reacting one mole of esters of wool wax acids and glycerol, in particular partial esters, with 0.5 to 30 moles preferable 2 to 15 moles of ethylene oxide.

The term "partial esters" is understood as meaning those esters of wool wax acids with glycerol in which only some, preferably about 40 to 60% of the original free hydroxyl groups of the glycerol are esterified with the wool wax acids, and which thus still contain free OH groups. These partial esters have, for example, OH numbers of about 120 to 164, saponification numbers of about 135 to 178 and dropping points in the range from about 46° to 48° C.

Ethoxylation products, which may contain up to 75 moles of ethylene oxide per mole of the wool wax or wool wax derivatives, of wool wax and certain wool wax derivatives, such as wool wax alcohols and wool wax acids which have undergone molecular distillation, are indeed already known, and some of these are marketed in the form of commercial products. These ethoxylation products, which have varying degrees of water-solubility (and in some cases are only dispersible in water), are preferably used as solubilizers, stabilizers, gelling agents and auxiliary emulsifiers in connection with other emulsifiers for the preparation of W/O and O/W emulsions. Where use as an O/W emulsifier is proposed in individual cases for these known products, depending on the length of the polyoxyethylene radical, this is almost always in connection with at least a small amount of wool wax, wool wax alcohols or other emulsifiers, cetyl alcohol or cetostearyl alcohol. Experiments have shown that it has not been possible to prepare O/W emulsions which are stable for a prolonged period using these known ethoxylation products as the sole O/W emulsifier in the customary amounts under conditions in practice.

In contrast, the ethoxylation products according to the invention, which are obtainable by reaction of one mole of esters of wool wax acids and glycerol, in particular partial esters, with 0.5 to 30 moles of ethylene oxide and which are obtained in the form of solid, waxy substances yellowish-white to yellow-brown in color, are all soluble in water and are excellent O/W emulsifiers and are outstandingly suitable for use by themselves for the preparation of stable O/W emulsions.

It was not possible to predict, and was therefore surprising, that, according to the invention, starting from a product with pronounced W/O emulsifier properties, a good emulsifier of the reverse type (O/W emulsifier) can be obtained by merely adding on very few ethylene oxide units (ester/ethylene oxide molar ratio of, for example, 1:2.9). In view of the known ethoxylation products of wool wax derivatives, in which an O/W emulsifier function appears or should appear only at a considerably higher number of ethylene oxide units in the molecule, this was in no way to be expected.

The invention furthermore relates to a process for the preparation of the novel O/W emulsifiers as claimed in claim 1, which comprises reacting wool wax acid glycerol esters, in particular the glycerol partial esters, with ethylene oxide in a manner which is known per se in the temperature range from about 120° to 200° C., preferably 120° to 160° C. and most preferably 130° to 150° C. preferably in the presence of an alkaline catalyst (c.f. M. J. Schick: "Nonionic Surfactants", New York (1967) and N. Schönfeldt: "Grenzflächenaktive Äthylenoxid-Addukte" ["Surface-active ethylene oxide adducts"], Stuttgart (1976)).

A procedure is followed in which the wool wax acid glycerol esters are introduced into a pressure vessel and a small amount of an alkaline catalyst, such as, for example, sodium hydroxide, potassium hydroxide, sodium methylate or potassium methylate, is added, and the mixture is then reacted with ethylene oxide, with exclusion of water. Temperatures in the range from about 120° to 200° C. preferably 120° to 160° C. and most preferably 130° to 150° C. are in general used here, and the addition of ethylene oxide is calculated such that the temperature neither falls below nor exceeds the range mentioned. The reaction is preferably carried out in the lower part of the temperature range mentioned, at about 120° to 160° C., most preferably 130° to 150° in order to avoid relatively severe discolorations of the reaction products. The reaction is advantageously carried out under increased pressure in an inert gas atmosphere, for example using nitrogen. If necessary, the particular reaction product obtained can be bleached with hydrogen peroxide.

The preparation of the wool wax acid glycerol esters used as the starting substance for the ethoxylation is known from German Pat. No. 2,023,786 and German Auslegeschrift 1,955,763.

It can be effected, for example, from wool wax acids and glycerol by customary esterification processes which proceed with the removal of water, as a rule at elevated temperature (up to about 230° C.), it being possible to promote the condensation by addition of water-binding agents or by suitable catalysts and by applying a gentle vacuum. By an appropriate reaction procedure in connection with a corresponding matching of the proportions of the reactants, it is possible to control the degree to which the OH groups of the starting substances are reacted (possibility of forming partial esters). The degree of esterification can be checked by the amount of water separated off or by determination of the acid and hydroxyl number of the reaction solution.

A further possibility of preparing the wool wax acid glycerol esters is transesterification of, for example, wool wax acid isopropyl esters with glycerol, which can advantageously be carried out in the temperature range from about 100° to 120° C. in the presence of a small amount of an alkaline catalyst.

Particularly good yields of wool wax acid glycerol esters or partial esters in the form of very pure, light-colored products are obtained if the esters are prepared by heating the mixture of wool wax acids and glycerol—without the addition of an esterification catalyst or an entraining agent—to a temperature of 200° to 250° C., while passing through hydrogen and in the presence of 0.01 to 5% of a hydrogenation catalyst (for example finely divided nickel, or palladium or platinum deposited on active charcoal), based on the total weight of the reactants, until the theoretically calculated amount of water has been separated off (German Auslegeschrift 1,955,763).

The process for the preparation of the novel O/W emulsifiers according to the invention is illustrated in more detail with the aid of the following examples:

EXAMPLE 1

145 g (0.35 mole) of a wool wax acid glycerol partial ester (saponification number 137) and 2.5 g (45 mmols) of potassium hydroxide powder were mixed with one another in a 1 liter glass autoclave which was designed to withstand 6 bar and was provided with an explosion-proof stirrer heating and a cooling device. The autoclave was filled with nitrogen and evacuated again three times. Thereafter, the mixture was dried at 90° C. under a water pump vacuum for one hour. Nitrogen was then forced in to a pressure of 0.5 bar and the contents of the autoclave were warmed to 130° C.

462 g (10.5 moles) of ethylene oxide were forced into the autoclave from a receiver with the aid of nitrogen at a rate such that a reaction temperature of 150° C. and a maximum pressure of 5 bar were not exceeded. After 150 minutes, the last ethylene oxide was forced into the autoclave. After a further 5 minutes, the end of the reaction was to be recognized by the drop in pressure and temperature. The reaction product was then cooled to 90° C. and degassed under a water pump vacuum for 30 minutes. After dropwise addition of 5.9 g of 30% strength hydrogen peroxide (1%, based on the amount of product) and subsequent stirring at 90° C. for 30 minutes, a yellow-colored product with an OH number of 76 and a saponification number of 28 was obtained.

EXAMPLES 2-8

The wool wax acid glycerol partial esters were reacted with various amounts of ethylene oxide by the procedure described in example 1.

The particular experimental conditions, reaction times and experimental results are shown in the following table, together with the corresponding data (OH number=OHN; saponification number=SN) from example 1:

TABLE

| Example | Amount of ester used (g) | Amount of EO used (g) | Molar ratio of ester/EO | KOH (g) | Reaction temp. (°C.) | Reaction time | OHN end product | SN end product |
| --- | --- | --- | --- | --- | --- | --- | --- | --- |
| 1 | 145 | 462 | 1:30 | 2.5 | 130°–150° | 14 hrs | 76 | 28 |
| 2 | 193 | 415 | 1:20 | 2.5 | 130° | 13 hrs | 96 | 37 |
| 3 | 209 | 326 | 1:14.5 | 2.5 | 140° | 10 hrs | 117 | 49 |
| 4 | 209 | 218 | 1:9.7 | 2.2 | 130° | 8 hrs | 141 | 62 |
| 5 | 360 | 194 | 1:5 | 2.2 | 135°–140° | 7 hrs | 177 | 82 |
| 6 | 314 | 98 | 1:2.9 | 2.0 | 135° | 5 hrs | 202 | 100 |
| 7 | 418 | 90 | 1:2 | 2.0 | 135° | 4 hrs | 213 | 108 |

TABLE-continued

| Example | Amount of ester used (g) | Amount of EO used (g) | Molar ratio of ester/EO | KOH (g) | Reaction temp. (°C.) | Reaction time | OHN end product | SN end product |
|---|---|---|---|---|---|---|---|---|
| 8 | 418 | 23 | 1:0.5 | 2.0 | 135° | 2½ hrs | 221 | 129 |

EO = Ethylene oxide

The invention furthermore relates to cosmetic agents which, in addition to the customary constituents, contain 1 to 15% by weight, preferably 2 to 6% by weight, based on the total formulation, of at least one compound according to claim 1.

The cosmetic agents according to the invention can be in various forms, in particular in the form of creams, milk and lotions. Depending on the particular intended use, they can contain the components customary in such agents in the proportions which are likewise customary, such as fatty alcohols with 12 to 18 carbon atoms (for example cetyl alcohol, myristyl alcohol or cetostearyl alcohol), medium-chain triglycerides, ester-like compounds (for example isopropyl myristate, isopropylpalmitate and propyleneglycol monomyristate), 1,2-propyleneglycol, mineral oil and triethanolamine (for neutralization of carboxyl groups). It has proved advantageous to limit the amount of fatty alcohols in the cosmetic formulation to not more than 6% by weight, based on the total composition, and to limit the amount of 1,2-propylene glycol to 5% by weight. The cosmetic agents can also contain 0.01 to 0.05% by weight, based on the total composition, of antioxidants, such as, for example, butyl hydroxyl toluene or butyl hydroxyanisole, preservatives, such as benzoic acid derivatives, and perfume, and, if appropriate, 1 to 4% by weight of a light stabilizer, such as 2-phenylbenzimidazole-5-sulphonic acid or salts thereof.

The particular amount of preservative and perfume to be employed can easily be determined by the expert by simple testing, according to the nature of the particular product.

The water content of the cosmetic agents according to the invention, which are stable O/W emulsions, can be 60 to 90%, preferably 80 to 90%, of the total composition.

The cosmetic products are prepared in the customary manner by mixing the constituents forming the oily phase and the constituents forming the aqueous phase independently of one another and warming them separately to about 75° C. The aqueous phase is then stirred into the oily phase, which is in the form of a melt at this temperature, and the mixture thus obtained (emulsion) is stirred until cold, perfumed at about 35° and homogenized once at 32° C. at stage 1 in a customary homogenizer. The emulsifier (polyethoxylated wool wax acid glycerol ester) is advantageously treated as a constituent of the oily phase and is mixed together and warmed with the other constituents of the oily phase.

The viscosity of the O/W emulsions can be influenced both by the consistency of the oily phase used and by the particular amount of water employed.

The following examples 9 to 11 are intended to illustrate the invention in more detail, without limiting it thereto, the constituents of the oily phase in each case being labeled with the letter O and those of the aqueous phase being labeled with the letter W.

EXAMPLE 9

(O/W sun milk)

| | |
|---|---|
| Emulsifier (product containing 14.5 moles of EO per mole of wool wax acid glycerol ester) | 3.00 g (O) |
| Cetyl alcohol | 1.00 g (O) |
| Propylene glycol monomyristate | 2.00 g (O) |
| Anti-foam agents ("Antischaum SH", Wacker: 0.04 g dissolved in 0.16 g of isopropyl myristate) | 0.20 g (O) |
| Antioxidant (butylhydroxytoluene) | 0.03 g (O) |
| Triethanolamine, pure | 0.20 g (O) |
| 2-Ethyl-hexyl p-methoxycinnamate | 2.00 g (O) |
| Isopropyl palmitate | 4.50 g (O) |
| Glycerol | 2.50 g (W) |
| 2-Phenylbenzimidazole-5-sulphonic acid (Na salt) ("Eusolex 232", Goodrich) | 1.00 g (W) |
| Acrylic acid polymer ("Carbopol 940", Goodrich) | 0.15 g (W) |
| Water, completely demineralized | 83.42 g (W) |
| Preservative | q.s. |
| Perfume | q.s. |
| | 100.00 g |

EXAMPLE 10

(O/W cream)

| | |
|---|---|
| Emulsifier (product containing 2.9 moles of EO per mole of wool wax acid glycerol ester) | 3.00 g (O) |
| Cetyl-stearyl alcohol | 6.00 g (O) |
| Mineral oil (3° E/50° C.) | 6.50 g (O) |
| Propylene glycol monomyristate | 2.00 g (O) |
| Anti-foam agent ("Antischaum SH20", formed from "Silikon-Antischaum SH", Wacker: 0.4 g + 0.16 g of isopropyl myristate) | 0.20 g (O) |
| Antioxidant (butylhydroxytoluene) | 0.03 g (O) |
| Triethanolamine, pure | 0.30 g (O) |
| 1,2-Propylene glycol | 2.50 g (W) |
| Acrylic acid polymer ("Carbopol 934", Goodrich) | 0.30 g (W) |
| Water, completely demineralized | 79.17 g (W) |
| Preservative | q.s. |
| Perfume | q.s. |
| | 100.00 g |

EXAMPLE 11

(O/W lotion)

| | |
|---|---|
| Emulsifier (product containing 9.7 moles of EO per mole of wool was acid glycerol ester) | 3.00 g (O) |
| Cetyl alcohol | 1.00 g (O) |
| Caprylic/capric acid triglyceride ("Miglyol 812", Dynamit Nobel AG) | 6.50 g (O) |
| Propylene glycol monomyristate | 2.00 g (O) |
| Anti-foam agent from "Silikon-Antischaum SH": 0.04 g + isopropylmyristate: 0.16 g | 0.20 g (O) |
| Antioxidant (butylhydroxytoluene) | 0.03 g (O) |
| Triethanolamine, pure | 0.15 g (O) |
| Glycerol | 2.50 g (W) |
| Acrylic acid polymer ("Carbopol 934" Goodrich) | 0.15 g (W) |
| Water, completely demineralized | 84.47 g (W) |
| Preservative | q.s. |
| Perfume | q.s. |

-continued

|  |
| --- |
| 100.00 g |

According to the above examples 9 to 11, high-quality O/W emulsions which have good stability even under prolonged storage under adverse conditions and exhibit a good tolerance by skin and mucous membranes and low sensitivity towards electrolytes are in all cases obtained.

The novel compounds according to the invention are thus useful O/W emulsifiers which have excellent superfatting properties and, in addition to having a very good emulsifying action, are good solubilizers for essential oils, aromas, vitamin oils and a large number of cosmetic and pharmaceutically active ingredients.

We claim:

1. A novel O/W emulsifier for cosmetic purposes based on polyethoxylated wool wax derivatives obtainable by reacting one mole of esters of wool wax acids and glycerol with 0.5 to 30 moles of ethylene oxide.

2. A novel O/W emulsifier of claim 1 wherein the esters reacted are partial esters.

3. An emulsifier of claim 2 wherein 2 to 15 moles ethylene oxide are reacted.

4. A cosmetic agent which contains, in addition to the pharmaceutically-acceptable carrier- and additive-materials, 1 to 15% by weight, based on the total formulation, of at least one compound as claimed in claim 1.

5. A cosmetic agent of claim 4 which contains 2 to 6% by weight, based on the total formulation, of at least one compound as claimed in claim 4.

6. A cosmetic agent of claim 4 where the pharmaceutically-acceptable carrier- and additive-materials are selected from the group consisting of fatty alcohols with 12 to 18 carbon atoms, medium-chain triglycerides, ester-like compounds, 1,2-propylenglycol, mineral oil, triethanolamine, antioxidants, preservatives, perfumes and light stabilizers.

* * * * *